United States Patent [19]

Medina et al.

[11] Patent Number: 5,100,670

[45] Date of Patent: Mar. 31, 1992

[54] USE OF A BACITRACIN FRACTION AS A GROWTH PROMOTING AGENT

[75] Inventors: Victor Medina, Bayside; Alfred Stracher, Rosiyn Estates; Leo Kesner, Brooklyn, all of N.Y.

[73] Assignee: Protor Co., Garden City, N.Y.

[21] Appl. No.: 457,114

[22] Filed: Dec. 26, 1989

[51] Int. Cl.$^5$ .................. A23K 1/165; A23K 1/17
[52] U.S. Cl. ...................... 424/442; 426/807; 514/3; 514/4; 514/21
[58] Field of Search ............. 514/3, 4, 21; 530/300, 530/303; 424/442; 426/807

[56] References Cited

U.S. PATENT DOCUMENTS 2,906,622  9/1959  Lewis ........................... 424/115
3,261,688  7/1966  McCutchan ................. 424/115

FOREIGN PATENT DOCUMENTS 0302445  2/1989  European Pat. Off. .

OTHER PUBLICATIONS

Tsuji et al., *Journal of Chromatography*, 99, 597–608 (1974).

*Primary Examiner*—Moezie, F. T.
*Attorney, Agent, or Firm*—Sprung, Horn, Kramer & Woods

[57] ABSTRACT

This application discloses an invention comprising a polypeptide fraction isolated from commerical bacitracin and which contains most if not all of the anti-insulinase activity of bacitracin while exhibiting few if any of the antibacterial properties. The invention herein described also involves the use of this polypeptide fraction given orally or if given parenterally either together (as composite) or in sequence as a means of treating diabetics. For such purposes, the insulin and anti-insulinase polypeptide fraction may be used as separate substances or chemically linked by a wide variety of chemical linking agents well known in the art. In addition to clinical uses, the application describes a method of using the polypeptide fraction as a growth promoter substance to be added to animal feed and also a composition useful for this purpose.

3 Claims, No Drawings

USE OF A BACITRACIN FRACTION AS A GROWTH PROMOTING AGENT

This application is a division of a pending application Ser. No. 559,445, filed July 23, 1990, which is a continuation of application Ser. No. 083,557, filed Aug. 7, 1987, now abandoned.

BACKGROUND OF THE INVENTION

The present invention relates to a way of enhancing the pharmacological effectiveness of the hormone insulin.

There now exist a number of non-insulin containing hypoglycemic agents and these have recently been reviewed (Asmal, et al., *Drugs*, 28, 62–78 (1984) and Wolf, et al., *Diabetologia*, 22, 456–463 (1982)). The Sulfonylurea drugs stimulate insulin secretion from the pancreas and exert other as yet undetermined peripheral effects; the biguanides inhibit gluconeogenesis, intestinal glucose absorption and mitochondrial oxidation; 2-bromopalmitate, ωmethyl 2-tetradecylglycerate, B807-27 and acyl aminocarnitines interfere with carnitine palmitoyl-transferase I enzyme which inhibits long-chain fatty acid oxidation.

Insulin is a polypeptide hormone of molecular weight 6,000 daltons which is secreted from the pancreas and is involved in the maintenance of glucose honmeostasis.

The diabetic patient must be treated with insulin or other hypoglycemic agents when insulin is either not produced (Type I diabetes) or inappropriately utilized (Type II diabetes) in order to deter the many harmful effects of elevated blood glucose levels and disturbed metabolism. It is clearly recognized that a variety of pathological defects may lead to the diabetic state. A review of these and the current strategies for treatment were recently reported (Diabetes Dialogue, *Am. J. Med.*, 79 (Suppl 2B), 1–44 (1985)).

Many diabetics require insulin injections one or more times a day to maintain their blood glucose levels within normal limits after meals.

Because injected insulin is quickly degraded by tissue proteinases, its effectiveness in lowering blood sugar is temporary. The destruction of insulin by the protease insulinase after injection occurs with a $t_{\frac{1}{2}}$ of approximately 40 minutes and, because of this short duration of action, many methods have been sought to inhibit this proteolytic inactivation of insulin in order to prolong its effectiveness. It has been reported in the literature that one such agent to inhibit insulinase in vitro is the antibiotic bacitracin.

Bacitracin is a polypeptide antibiotic which has been found useful as an antimicrobial agent in humans and as a growth promoter in animals. The antimicrobial properties of commercial bacitracin resides mainly in one fraction, bacitracin A. It works best against gram-positive bacteria by disturbing their membrane function, cell wall synthesis and protein metabolism.

The most widely used food additives for growth promotion are the zinc bacitracin and bacitracin methyldisalicylate forms of this antibrotic. While it is generally accepted that the addition of low levels of antibiotics to feeds can improve animal growth and product, the mechanism of action is unknown (Froyshov, *Drugs and Pharmaceutical Science*, Chapt. 24, 665–694 (1984)).

It has been known for many years that the commercial preparation is a mixture of at least 20 different compounds with bacitracins A and F representing respectively 65–70% and 15–20% of the total content (Tsuji, et al., *J. Chromatog.*, 99, 597–608 (1974). In addition to its antibiotic properties, the commercial preparation of bacitracin has been shown to be capable of inhibiting the degradation of insulin in a variety of in vitro experimental situations such as with isolated rat hepatocytes and adipocytes (Duckworth, et al., *Endocrinology*, 108, 1142-1147 (1981), Roth, et al., *Biochem. Biophys. Res. Commun.*, 98, 431–438 (1981) and Peavy, et al., *Diabetes*, 34, 217–221 (1985)). Thus bacitracin was shown to potentiate the action of insulin on glucose utilization.

SUMMARY OF THE INVENTION

In accordance with the present invention there has been isolated from commercial USP bacitracin a fraction, comprising less than about 20%, preferably less than about 10% and most preferably less than about 5%, of the weight of the bacitracin. This fraction is apparently not antibiotically active but is disproportionately high in anti-insulinase activity relative to the starting bacitracin mixture.

It can be administered by itself which is alone adequate in some types of diabetes where the body manufactures enough insulin. In most instances, however, this material will be administered along with insulin, either admixed therewith or covalently linked thereto. The insulin can be pre-modified with other protease inhibitors prior to its admixture or reaction with the novel bacitracin fraction.

In accordance with yet another aspect of the invention, the novel bacitracin fraction can be used in animal feeds as a growth promoter. Bacitracin is known to enhance animal growth but is undesirable in general feeds because its widespread use will result in exposure of animals and consumers of animals to bacteria resistant to bacitracin. Use of the non-antibiotic fraction overcomes this problem.

Apart from its growth promotion, the active fraction is itself hypoglycaemic. Apparently it keeps insulin within the human or animal body for a longer period of time, i.e. inhibits its decomposition.

The use of the active insulinase inhibitor fraction will overcome the problems associated with the antibiotic resistance which sometimes develops in individuals exposed to food products containing trace amounts of antibiotics in the food they consume.

DESCRIPTION OF THE PREFERRED EMBODIMENTS

To obtain the desired polypeptide fraction, bacitracin is produced in conventional manner. The principal components have been designated bacitracin A and F, but these exhibit substantially no anti-insulinase activity. Accordingly, the bacitracin is subjected to fractionation in various ways and the non-A, non-F component constitutes the desired material which can be further fractionated and/or purified.

The fractionations advantageously involve selective or preferential adsorption and/or elution from conventional adsorbents such as Sepharose, activated carbon, ion exchangers, and the like, employing selective solvents and eluants, buffers, etc. Thus which fraction will be held more tenaciously can be adjusted by choice of conditions.

The recovered fractions are isolated and those not exhibiting substantial anti-insulinase activity are discarded. The desired fraction is believed to have a molecular weight of about 1400, approximately the same as bacitracin A or F. Their anti-insulinase and antibacterial activities can be assayed in conventional manner. For example, the insulinase inhibitory activity was measured according to the method of Duckworth, et al., *Proc. Nat. Acad. Sci.*, 69, 3698-3702 (1972) and the antibacterial activity by the method of Patrick, et al., *Antibiotics and Chemotherapy*, 1, 133-137 (1951).

Administration of this purified fraction will combat insulinase in a subject's system. Thus, in the case of patients whose bodies produce enough insulin but whose problem is excessive insulinase, this material itself may suffice. However, where insulin injections are required, the purified fraction should be administered either prior to or along with insulin. This can be at different times and in varying proportions depending on the patient's condition.

The materials are advantageously administered together and, further, advantageously covalently coupled to one another in a manner which does not destroy their effectiveness.

The insulin is advantageously present in about 1 to 1 and preferably about 0.2 to 20 times the weight of the polypeptide fraction.

When present, the covalent link can be derived from a polyvalent, preferably divalent, compound such as a dicarboxylic acid, a diamine, an aminocarboxylic acid, a dialdehyde, a diimide, a diisocyanate, etc. The length of the chain can vary but advantageously is from about 4 to 20 atoms long. Suitable couplers include, for example, $\epsilon$-aminocaproic acid, glutaraldehyde, carbodiimide, hexamethylene diisocyanate, phosgene, and the like. A variety of available methods have been reported and collected into several recent reviews.(Kennedy et al, *Clinica Chem. Acta*, 70, 1-31 (1976); Method Enzymology 112, Pt. A (1985) Ch. 16, 17, 19, 20, 21, 23).

The amount of couplers can be varied widely from none up to about 10% or even 20% by weight of the combined insulin and polypeptide fraction. Such coupling can be effected in conventional manner either by mixing all three ingredients in a solvent or stepwise by first reacting the coupler with one component and then reacting the coupled intermediate with the other component. Then the desired material is freed of by-products and/or impurities and is ready for use, alone or with conventional additives such as buffers, fillers, solvents, stabilizers, etc.

The novel fraction can be administered orally, parenterally or by any other suitable means of treatment. In all cases, administration may be either concurrent with insulin treatment, prior to or following an appropriate dose of insulin.

The exact dosage will depend on the patient's condition, body weight, etc. About 1 to 100 units and preferably about 2 to 20 units of insulin per day is suitable for an adult, although this may be exceeded or diminished in special cases, as called for by the physician.

When the polypeptide fraction is used as an animal feed supplement, it can be present in from about 1 to 100 ppm and preferably about 3 to 50 ppm by weight but can be further diluted by the animal's feed. The amount administered depends upon the animal and its stage of development.

The invention will be further described in the following examples wherein all parts are by weight unless otherwise expressed.

EXAMPLE 1

A 350 ml bed volume of CM-Sepharose in a packed column (2.8×56 cm) was equilibrated with 0.05M ammonium acetate, pH 4.5. One gram of commercial bacitracin dissolved in 50 ml of buffer was applied to the packed column. The material was eluted with 2 liter of equilibrating buffer followed by 350 ml of 1M ammonium acetate pH 4.5 buffer. Five ml fractions were collected and absorbance measurements at 252, 280 and 290 nm were made. In addition, insulinase inhibitory activity measurements were made on each peak. Bacitracins F and A, exhibiting negligible insulinase inhibitory activity, were eluted as distinct peaks with the first buffer. The peaks were collected, lyophilized, weighed and dissolved in water at 5 mg/ml concentration for specific activity measurements. The material collected with the second buffer contained 5-10% of the total weight of the applied material and 90% of the total insulinase inhibitory capacity. The specific activity of this material was 10-12 times that of the starting commercial material. HPLC and gel filtration studies revealed that this fraction contains several components of varying insulinase inhibitory capacity.

EXAMPLE 2

10 $\mu$mol (mw=1400 approximately)) of the active fraction of Example 1 are dissolved in 1 ml dry dimethylformamide (DMF). To this 20 $\mu$mol 1-ethyl-3,3 dimethylaminopropylcarbodiimide (CDI) and 20 $\mu$mol of N-hydroxysuccinimide are added. The mass is permitted to react for 2 hours at room temperature, and then the product is coupled with insulin by adding, in a dropwise manner with stirring, 1.5 $\mu$moles of insulin dissolved in 30 ml of 0.05M sodium acetate solution. After 2 hours at room temperature the product is supplied to a 50 cm chromatographic column 3.5 cm in diameter filled with Sephadex LH20 support material. Elution can be effected with 0.9% NaCl solution, collecting fractions. Those fractions which show anti-insulinase activity can be used clinically.

EXAMPLE 3 a) 10 $\mu$mol of the active fraction of Example 1 are treated with 150 nmoles of N-hydroxysuccinimide and 500 $\mu$mols of carbodiimide and 70 $\mu$moles of diaminobutane. The reaction is allowed to proceed at room temperature for 4 hours and the mixture is separated by Sephadex chromatography as in Example 2 and the various fractions are tested for amino functional groups with picrylsulfonic acid. The first amino-containing fraction is the diaminobutane derivative of bacitracin. This fraction is lyophylized.

b) 10 $\mu$moles of insulin are dissolved in 0.01M HCl to a concentration of 0.6 mg/ml, carbodiimide is introduced to a concentration of 0.1M and the pH is adjusted to 7.0 by dilute NaOH. The product of (a) is dissolved in 2 cc of water and added dropwise to the insulin solution where it is kept at pH 7 for 1 hour.

The products of Examples 2 and 3 can be isolated by Sephadex chromatography and the active fraction lyophilized prior to administration of an appropriate amount.

It will be understood that the specification and examples are illustrative but not limitative of the present invention and that other embodiments within the spirit and scope of the invention will suggest themselves to those skilled in the art.

What is claimed is:

1. An animal growth-promoting composition comprising an edible feed base and an animal growth-promoting effective amount of a polypeptide fraction isolated from bacitracin and, on a weight basis, exhibiting at least 5 times the anti-insulinase activity of the bacitracin, the fraction having a molecular weight of about 1400, being obtainable by adsorption from bacitracin on CM-Sepharose and subsequent elution and being substantially free of A and F bacitracin components.

2. A method of promoting the growth of animals which comprises administering to the animals a growth-promoting effective amount of a composition according to claim 1.

3. A method of promoting the growth of animals which comprises administering to the animals a growth-promoting effective amount of a polypeptide fraction isolated from bacitracin and, on a weight basis, exhibiting at least 5 times the anti-insulinase activity of the bacitracin.

* * * * *